United States Patent

Otsuka et al.

[11] 4,152,232
[45] May 1, 1979

[54] OXYGEN CONCENTRATION DETECTOR

[75] Inventors: Yasuhiro Otsuka; Ryuzo Hori; Kiyoshi Uchida; Toshinobu Furutani, all of Toyota, Japan

[73] Assignee: Toyota Jidosha Kogyo Kabushiki Kaisha, Toyota, Japan

[21] Appl. No.: 810,886

[22] Filed: Jun. 28, 1977

[30] Foreign Application Priority Data

Dec. 25, 1976 [JP] Japan .................... 51-157026

[51] Int. Cl.² .................... G01N 27/46
[52] U.S. Cl. .................... 204/195 S; 204/1 T
[58] Field of Search .................... 204/15, 195 S

[56] References Cited

U.S. PATENT DOCUMENTS

| | | | |
|---|---|---|---|
| 3,619,381 | 11/1971 | Fitterer | 204/195 S |
| 3,904,486 | 9/1975 | Faurschou et al. | 204/195 S |
| 3,960,693 | 6/1976 | Weyl et al. | 204/195 S |
| 4,040,930 | 8/1977 | Dillon | 204/195 S |

Primary Examiner—T. Tung
Attorney, Agent, or Firm—Brisebois & Kruger

[57] ABSTRACT

The present invention relates to an oxygen concentration detector to be used in a system which can simultaneously dispose of the three harmful elements in automotive emissions, i.e., unburnt hydrocarbons (unburnt HC), carbon monoxide (CO) and nitrogen oxides (NOx) through reaction with catalyst. In said detector an oxygen concentration cell comprises a solid electrolyte of a special ceramic material characterized by oxygen ion-conductivity; and the oxygen concentration of a measured gas can be analyzed by measuring the electromotive force generated through a difference in the oxygen partial pressure between the measured gas and a reference gas.

5 Claims, 8 Drawing Figures

OXYGEN CONCENTRATION DETECTOR

BACKGROUND OF THE INVENTION

In conventional detectors the equilibrium oxygen partial pressure of the atmosphere or of a metal and its metal oxide is utilized as the reference gas, but the following drawbacks are recognized with these detectors. For instance, in a detector which utilizes the atmosphere as the reference oxygen partial pressure, an air duct is required and the infiltration of water, sand or salt etc. into said air duct has to be prevented, which renders the detector complicated in structure. If a mixture of a metal and its metal oxide is used for the source of the reference oxygen partial pressure such as Ni/NiO, Cu/CuO, Co/CoO, Fe/FeO reacts with the vessel of solid electrolyte and accordingly a long continued use of the detector with stability cannot be expected.

In the case of a detector using a solid reference oxygen pole, in which a lead wire is buried in the mixture of a metal and its metal oxide to transmit the electric output, a high internal resistance of the mixture itself or a high contact resistance between said mixture and the lead wire causes deterioration of the low temperature performance when the detector is assembled in the system.

SUMMARY OF THE INVENTION

The present invention relates to an improvement in an oxygen concentration detector to measure the oxygen content in the auto emission.

The main object of the present invention is to provide an oxygen concentration detector characterized in that metal electrodes are formed on the inside and outside surfaces of a sintered solid electrolyte; a sintered mixture of a metal and its metal oxide and said sintered solid electrolyte are separated to prevent contact from each other; and an equilibrium system of said metal and its metal oxide is taken as the source of the reference oxygen partial pressure.

Another object of the present invention is to provide an oxygen concentration detector characterized in that said sintered mixture is separated from said sintered solid electrolyte by means of fibrous material such as silica wool, alumina wool, mullite wool, sintered inorganic material, sintered $Al_2O_3$, sintered $SiO_2$, sintered mullite or air space.

The other objects of the present invention will become apparent from the description of embodiments of the present invention.

DETAILED EXPLANATION OF THE INVENTION

Figure 1:
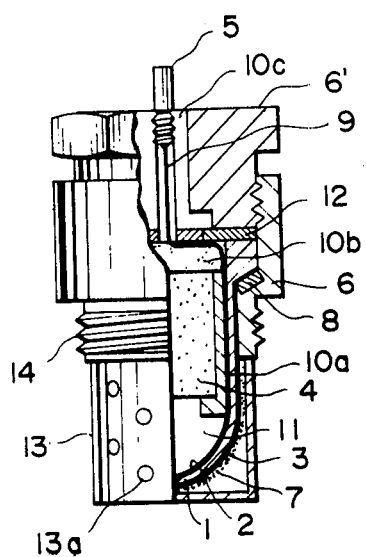
FIG. 1 is a partial fragmentary sectional view of an oxygen concentration detector according to the present invention.

After strenuous efforts to eliminate the above-mentioned drawbacks and develop a high precision oxygen concentration detector the present inventors have developed an improved oxygen concentration detector simplified in structure which can maintain good low temperature performance even when assembled in a system and can function with stability in long continuous service.

The structure of the invented detector will be described with reference to FIG. 1, which is a partial fragmentary section view of the detector.

As seen from the figure, the detector according to the present invention consists of a solid electrolyte vessel 1 made of an oxygen ion-conductive ceramic material (hereinafter to be called the vessel); metal electrodes 2, 3 formed on the inside and outside surface of the vessel 1; a sintered mixture 4 of a metal and its metal oxide to become the source of the reference oxygen partial pressure, which is spaced from said metal electrode 2 in said vessel 1 (to be called the sintered mixture hereafter); terminal means 5 for the outputs of said metal electrode 2; and detector holders 6, 6'.

In the detector according to the invention, the metal electrode 3 is externally provided with a porous coating layer 7 of inorganic material, such as alumina, and the electric output terminal of said electrode 3 is connected to the detector holder 6 through a conductive sheet 8 such as a graphite sheet. On the other hand the internal surface of metal electrode 2 in the vessel is connected to said terminal 5 by the lead wire 9 without contacting either of the detector holders 6, 6'.

Furthermore, the sintered mixture 4 is surrounded by a non-conductive spacer 10a which does not react with the metal electrode 2 and an air space 11 for the purpose of isolating the sintered mixture 4, while above said sintered mixture 4 are provided non-conductive spacers 10b and 10c separated by a non-conductive spacer 12 to prevent the external air from invading the air space 11 of the vessel.

In the detector of the present invention, the accuracy of the detector according to the invention will not be affected even when the space 11 of the vessel is filled with a porous substance. In the figure, 13 is a protective sleeve with air holes 13a. Said protective sleeve 13, being welded to the detector holder 6, serves to protect the vessel 1 from thermal or mechanical shock etc. The member 14 is a fitting screw for the detector body.

The vessel 1 of the present invention has only to be made of anything which is oxygen ion-conductive, which may be, for instance, $ZrO_2$-$MgO$ or $CaO$, $Y_2O_3$ etc. The non-conductive spacers 10a–10d have only to be made of anything which does not react significantly with the sintered mixture 4, which may be, for instance, alumina, silica or mullite. For the spacer 10d, in particular, inorganic fibers such as silica wool, alumina wool or mullite wool, etc., are suitable. The non-conductive spacer 10a is shaped as illustrated in the oblique views of FIGS. 2–5(A). When three such spacers are employed as illustrated in FIG. 5(A), they serve to hold the top and bottom of the sintered mixture 4 in the vessel 1 as illustrated in FIG. 5(B).

Several specific embodiments of the present invention will now be described.

EXAMPLE 1

A tubular member having one end sealed with $ZrO_2$ which had been stabilized by addition of 10 mol % of $Y_2O_3$ was prepared. Said member was sintered; etched with hydrofluoric acid; chemically plated with chloroplatinic acid and hydrogenated sodium borate; and thus a vessel with platinum coating formed on the inside and outside surfaces was obtained.

Said vessel was electroplated in a commercial plating solution, thereby forming a platinum electrode about $1\mu$ in thickness on said platinum coats.

Meanwhile, commercial FeO and commercial carbonyl cracked iron powder were blended in equal mols and the mixture thus obtained was fired at 900° C. in an argon atmosphere for 3 hours, thus yielding a sintered mixture with a porosity ratio of 30%. On the other hand, using alumina powder with $SiO_2$ added as a binder, a spacer having the profile indicated in FIG. 2 was obtained and fired in the air at 1800° C. for 24 hours.

Next, the vessel was charged with the non-conductive alumina spacer and the sintered mixture. Thereupon, the external platinum electrode was connected to the detector holder by a graphite sheet, while the internal platinum electrode was connected to the outside by a non-conductive alumina spacer, after a platinum wire had been platinum-pasted to said electrode. To assure air-tightness of the vessel, the non-conductive spacer was set in place using an inorganic bonding agent.

Figure 3:
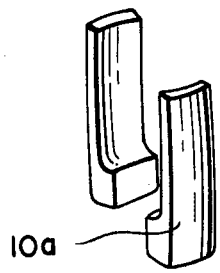
FIGS. 2 to 4 and 5A are oblique views of a non-conductive spacer to be used in the present invention.
Figure 4:
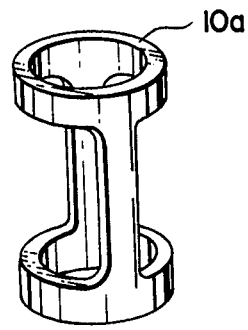
Figure 5A:
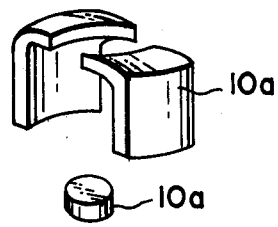
Figure 5B:
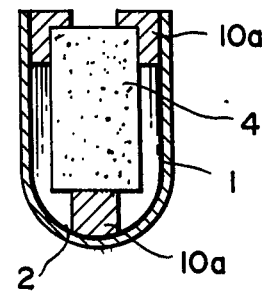
FIG. 5B shows the non-conductive spacer of FIG. 5A in a vessel.

In addition to the detector thus constructed, others with the spacer varied in profile as shown in FIGS. 3, 4 and 5 may be used.

The various kinds of detectors according to said present invention were subjected to heat resistance tests in which they were heated at 1000° C. in the air until the electromotive force in them reached 0.5V, thereby checking their service life. The service life data as shown by these heat resistance tests are listed in the following table 1.

EXAMPLE 2

Instead of alumina powder, as in Example 1, silica ($SiO_2$) was employed as the material of which the spacer was made, and the firing temperature was set at 1600° C.; otherwise the conditions for preparing the detector were the same as in Example 1. The spacer profile was varied as in FIGS. 3, 4, 5, just as in Example 1, and the service life of the detector was checked by the same heat resistance test as in Example 1, the results being summarized in the following table 1.

EXAMPLE 3

Instead of alumina powder, as in Example 1, mullite was employed as the material of which the spacer was made and the firing temperature was set at 1600° C.; otherwise the conditions for preparing the detector were the same as in Example 1. The spacer profile was varied as shown in FIGS. 3, 4, 5, just as in Example 1, and the service life of detector was checked by the same heat resistance test as in Example 1, the results being summarized in the following table 1.

EXAMPLE 4

Figure 2:
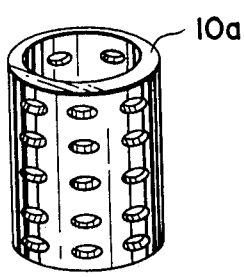
Figure 6:
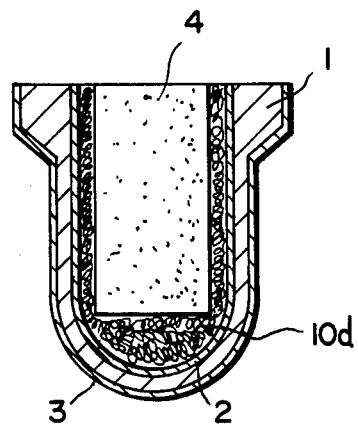
FIG. 6 is a diagram illustrating the separation of the internal metal electrode from the sintered mixture in the fourth embodiment of the present invention.

In this example, three kinds of detectors were prepared in the same way as in Example 1, except that, as illustrated in FIG. 6 showing the manner of separation of the sintered mixture from the internal metal electrode, instead of separating them by means of the non-conductive spacer 10a in FIG. 2, the sintered mixture, surrounded with a ceramic fiber such as alumina wool, silica wool or mullite wool, was charged into the vessel so that the sintered mixture could be held elastically without contacting the internal platinum electrode by the elasticity of said ceramic fiber. These detectors were subjected to the same test as in Example 1, the results being summarized in the following table 1.

EXAMPLE 5

Figure 7:
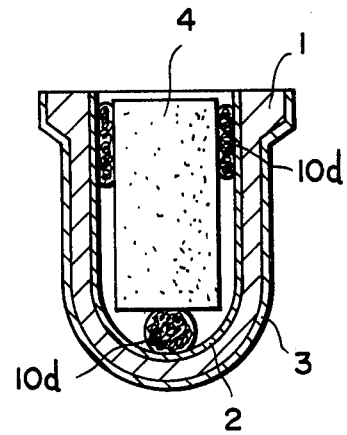
FIG. 7 is a diagram illustrating the separation of the internal metal electrode from the sintered mixture in the fifth embodiment.

In this example, three kinds of detectors were prepared in the same way as in Example 1 except that, as illustrated in FIG. 7 showing the manner of separation of the sintered mixture from the internal metal electrode, instead of separating them with the non-conductive spacer 10a as in FIG. 1, the sintered mixture surrounded at only the top and bottom with a ceramic fiber such as alumina wool, silica wool or mullite wool, was charged into the vessel so that the sintered mixture could be elastically held without contacting the internal platinum electrode by the elasticity of said ceramic fiber. These detectors were subjected to the same test as in Example 1, the results being summarized in the following table 1.

REFERENCE EXAMPLE

A detector was prepared in the same way as in Example 1 except that without the spacer in Example 1, the sintered mixture was allowed to contact the internal platinum electrode. The detector thus obtained was subjected to the same test as in Example 1, the results being summarized in the following table 1.

TABLE 1

| Separation means | Service Life of Detector in Heat Resistance Test (hours) | | | | | Reference |
|---|---|---|---|---|---|---|
| | Examples | | | | | |
| | 1 | 2 | 3 | 4* | 5** | |
| Spacer in FIG. 2 | 400 | 390 | 400 | — | — | 180 |
| Spacer in FIG. 3 | 410 | 400 | 390 | — | — | — |
| Spacer in FIG. 4 | 420 | 380 | 400 | — | — | — |
| Spacer in FIG. 5 | 410 | 400 | 410 | — | — | — |
| Silica wool | — | — | — | 380 | 400 | — |
| Alumina wool | — | — | — | 390 | 420 | — |
| Mullite wool | — | — | — | 400 | 400 | — |

Notes-
*Sintered mixture and internal platinum electrode separated from each other in the manner of Figure 6.
**Sintered mixture and internal platinum electrode separated from each other in the manner of Figure 7.

The table shows how substantially the life of the detectors according to the present invention is improved over that of the one of the reference example. In each of the invented detectors the electromotive force at 1000° C. is close to the theoretical value of 0.9V, which shows that the invented detector has as good performance as a conventional detector.

Thus the detector according to the present invention, which is simplified in structure as illustrated in the drawings but as accurate as a conventional detector, and can function with stability for a longer time than a conventional detector, can be said to have a high commercial value.

What is claimed is:

1. A vehicle exhaust gas oxygen concentration detector comprising:
   (a) a solid electrolyte vessel made of a ceramic material having oxygen ion-conductivity;

(b) a pair of metal electrodes formed respectively, on the inner and outer surface of said solid electrolyte vessel;

(c) a sintered mixture of a metal and its metal oxide, which constitutes a reference oxygen partial pressure source within said solid electrolyte vessel and separated from said metal electrodes;

(d) a holder for said solid electrolyte vessel which is electrically connected to the metal electrode on the outer surface of said solid electrolyte vessel;

(e) an output terminal electrically connected to the metal electrode on the inner surface of said solid electrolyte vessel, and (f) an electrically non-conductive spacer in said electrolyte vessel disposed between the sintered mixture and the inner surface of the vessel for supporting said sintered mixture both axially and radially of said vessel to prevent movement of said sintered mixture within said vessel due to vibrations of the vehicle, said spacer being of a material which is non-reactive with said metal electrode on the inner surface of the vessel.

2. Oxygen concentration detector as claimed in claim 1, in which said non-conductive spacer is made of a fibrous substance.

3. Oxygen concentration detector as claimed in claim 1, in which said non-conductive spacer is made of a material selected from the group consisting of silica wool, alumina wool and mullite wool.

4. Oxygen concentration detector as claimed in claim 1, in which said non-conductive spacer is made of a sintered inorganic substance.

5. Oxygen concentration detector as claimed in claim 1, in which said non-conductive spacer is made of a material selected from the group consisting of sintered $Al_2O_3$, sintered $SiO_2$ and sintered mullite.

* * * * *